(12) United States Patent
Ysebaert

(10) Patent No.: US 6,364,908 B1
(45) Date of Patent: Apr. 2, 2002

(54) METHOD AND INSTRUMENTS FOR STRETCHING SKIN GRAFTS

(75) Inventor: Willem Marie Ysebaert, Oss (NL)

(73) Assignee: Burncare B.V., Beberwijk (NL)

( * ) Notice: Subject to any disclaimer, the term of this patent is extended or adjusted under 35 U.S.C. 154(b) by 0 days.

(21) Appl. No.: 09/284,544

(22) PCT Filed: Oct. 14, 1997

(86) PCT No.: PCT/NL97/00574

§ 371 Date: Aug. 4, 1999

§ 102(e) Date: Aug. 4, 1999

(87) PCT Pub. No.: WO98/16159

PCT Pub. Date: Apr. 23, 1998

(30) Foreign Application Priority Data

Oct. 15, 1996 (NL) ............................................. 1004276

(51) Int. Cl.[7] ............................................. A61B 17/08
(52) U.S. Cl. ..................... 623/15.12; 606/215; 623/909
(58) Field of Search .......................... 623/15.11, 15.12; 606/216, 151, 132, 131, 215; 600/36

(56) References Cited

U.S. PATENT DOCUMENTS

| | | | | |
|---|---|---|---|---|
| 3,470,782 A | | 10/1969 | Acker | ........................ 83/451 |
| 4,373,519 A | * | 2/1983 | Errede et al. | ................ 604/367 |
| 4,773,418 A | * | 9/1988 | Hettich | ........................ 606/132 |
| 4,927,410 A | | 5/1990 | Kovacs | ........................ 600/36 |
| 5,234,462 A | * | 8/1993 | Pavletic | ........................ 606/216 |
| 5,571,138 A | * | 11/1996 | Blomqvist et al. | .......... 606/216 |
| 5,686,303 A | * | 11/1997 | Korman | ........................ 435/325 |
| 5,914,264 A | * | 6/1999 | Korman | ........................ 623/15 X |
| 5,972,022 A | * | 10/1999 | Huxel | ........................ 606/216 |

FOREIGN PATENT DOCUMENTS

| | | |
|---|---|---|
| DE | 9403937.2 | 3/1994 |
| SU | 2018272 | * 8/1994 |
| WO | WO84/02464 | 12/1983 |

* cited by examiner

Primary Examiner—Bruce Snow
Assistant Examiner—Brian E Pellegrino
(74) Attorney, Agent, or Firm—Skjerven Morrill & MacPherson; Alan H. MacPherson

(57) ABSTRACT

A method for spreading skin grafts, wherein the skin grafts are placed on an elastic membrane, after which the membrane is stretched in at least two directions substantially perpendicular to each other and the skin grafts present on the membrane are spread. A spreading means, a stretcher and a membrane to be used therewith, as well as to a method for applying skin grafts to a burn.

16 Claims, 3 Drawing Sheets

METHOD AND INSTRUMENTS FOR STRETCHING SKIN GRAFTS

FIELD OF THE INVENTION

The present invention relates to a method for spreading skin grafts and to spreading means, a stretcher and a membrane to be used therewith, as well as to a method for applying skin grafts to a burn.

BACKGROUND OF THE INVENTION

In practice a method for spreading skin grafts often comprises placing skin grafts on gauze which has been pre-folded in two directions in advance (pleat). To that end an adhesive is applied to the skin grafts on the pre-folded gauze, and after the adhesive has dried the folded gauze is stretched in two directions, as a result of which the distance between the skin grafts is increased. This has led to the situation wherein the small squares, viz. the cut skin grafts, are arranged in regularly spaced-apart (about 5 mm) relationship, with the cutting side facing upwards. Then the folded bandage is laid loosely on the excised area, provided with perforations for drainage, and subsequently fixed in position by means of gauze. In this manner an increase in area of about nine times the original dimension is obtained. The drawback of such a method is that after about one week the gauze is removed under an anaesthetic and can be replaced by donor skin. Another drawback is the fact that it takes a considerable amount of routine to be able to carry out such a method. In addition to that the use of an adhesive is undesirable, because it has an adverse effect on the production of large amounts of skin grafts.

In addition to that it is known from International patent application WO 92/15251 to stretch skin, using stretching means to be fitted to a patient under local anaesthesia. The extra skin which is formed by said stretching in conjunction with the natural growing power of the human skin is cut away and used for transplantation purposes. A drawback of such a method is the fact that it takes surgery to obtain additional skin.

SUMMARY OF THE INVENTION

Now a method for spreading skin grafts has been found which does not exhibit the above drawbacks. In addition to that the method which has been discovered can be carried out by medical staff who have not been specially trained for this purpose.

The method as referred to in the introduction is characterized in that the skin grafts are placed on an elastic membrane, after which the membrane is stretched in at least two directions substantially perpendicular to each other and the skin grafts present on the membrane are spread.

A method for forming skin grafts is known from Dutch patent application No. 1004276, which document may be considered to be incorporated herein. Although it is possible to use any other known method for forming skin grafts, such as the method known from International patent application WO 84/02464, it is preferred to use the method according to Dutch patent application No. 1004276.

It is preferred to use as a membrane a carrier which is used for forming the skin grafts. According to this method an increase in area of about nine times the original dimension is achieved. From practice it has become apparent that in this manner little auto transplant or autogenous skin is needed to cover large defects on burn patients.

The present invention furthermore relates to spreading means to be used for increasing the distance between the skin grafts, which means is characterized in that said spreading means comprises an elastic membrane which is connected to arms which are capable of movement in at least two directions in the same plane, which arms are made of a material which is less elastic than the material of which the membrane is made, as well as a base member, which can be connected to said arms.

In a preferred embodiment said spreading means comprises four to eight arms which are capable of movement in opposite directions in the same plane, which arms can be connected to the base member, after which the arms are extended. Since the material of which the membrane is made is more elastic than the material of which the arms are made, the surface area of the membrane will be considerably extended as a result of the extension of the arms. Thus the distance between the skin grafts will be increased and the spreading of the skin grafts has been achieved.

In a special embodiment of the present invention the skin grafts formed from skin, which adhere to a carrier, are transferred to the elastic membrane of the spreading means by transport means operating at a sub-atmospheric or reduced pressure. A transport means operating at a sub-atmospheric pressure is known from International patent application WO 84/02464. The skin grafts adhering to the transport means are removed therefrom by releasing the sub-atmospheric pressure, possibly in conjunction with the moving of pins from an ejector through the apertures of the transport means, or by applying a slight overpressure by using compressed air, after which the skin grafts land on the membrane, in particular on the central part thereof. Then the elastic membrane is stretched by moving the arms of the assembly of membrane and arms, which is according to the present invention preferably carried out by using wind-up means connected to the base member, which wind-up means are rotatably mounted therein. Such wind-up means can be connected to the arms, as a result of which the membrane connected to the arms can be stretched and the skin grafts present on the membrane can be spread. The assembly of membrane and arms is preferably moved by connecting the arms to the base member via wind-up rods, which wind-up rods can be moved by means of a ratchet wrench and a gear wheel, for example. Further extension of the membrane by means of such wind-up rods, whereby the arms are wound on the wind-up rods, will result in the distance between the skin grafts being increased. In certain embodiments of the present invention the arms may already be attached to the base member, however, and the membrane may have to be connected to the arms so as to spread the skin grafts present on the membrane. The advantage of this is that the membrane can be disposed of after use and be replaced by a new membrane. If the membrane and the arms are made in one piece, the arms must be connected to the wind-up rods, and the assembly of membrane and arms can be removed and be replaced after use.

It is preferred to make the membrane of an elastic material having a rough surface or porous material in order to ensure a minimal adherence of the skin grafts to the membrane. A woven or knit material is suitable as the porous material for the membrane. The advantage of a material of this type is that when a force is exerted thereon, the yarns are pulled apart, as a result of which the desired space between the yarns, or the desired porosity, is achieved. In addition to that it must be possible to subject the membrane to a sterilization treatment. In a special embodiment of the spreading means the space under the membrane is provided with a connection for sub-atmospheric pressure and compressed air. Preferably also an ejector is mounted in such a space. It should be apparent that spread skin grafts can be removed from the spreading means by tweezers, but this is very time-consuming, and in practice it is preferred to use the transport means described in Dutch patent application No. 1004276.

In a special embodiment of the spreading means according to the present invention a stretcher is provided, which can be connected to the base member. The arms of the elastic membrane can be clamped down in such a stretcher, thus making it possible to maintain the stretched condition of the arms, which is obtained by stretching the arms, using the above-described wind-up means. Thus the stretcher with the spread skin grafts present on the membrane can be detached from the base member and be transported to the intended location. The base member will then be available again for spreading a new batch of skin grafts in accordance with the method of the present invention. The advantage of using such a stretcher is that large amounts of spread skin grafts can be obtained at short intervals, in particular by using only one base member.

In a preferred embodiment of the present invention the stretcher to be used in spreading skin grafts comprises at least two clamping means, in which the membrane and/or the arms connected to the membrane can be clamped down. More in particular the number of arms connected to the membrane corresponds with the number of clamping means present in the stretcher, preferably the number of clamping means is four to eight. The clamping means according to the present invention preferably comprises a base member and a top member, whereby said base member and said top member exhibit a clamping action.

The present invention furthermore relates to a method for applying skin grafts to a burn, which method is characterized in that a skin-like material is placed on the spread skin grafts, after which the skin grafts adhering to said material are applied to the burn. Preferably a gauze of plastic material is used as a suitable skin-like material. More in particular donor skin is used. When the skin grafts are covered with donor skin, the healing process is accelerated, which is desirable in practice.

In another embodiment an adhesive is first applied to the spread skin grafts, after which a skin-like material is placed on the skin grafts provided with an adhesive, and the whole is subsequently applied to the burn. The advantage of applying an adhesive is that the spread skin grafts adhere to the material in an advantageous manner, as a result of which no skin grafts are lost.

BRIEF DESCRIPTION OF THE DRAWINGS

The present invention will be explained in more detail hereafter by means of the appended examples in conjunction with the illustrated drawings.

DETAILED DESCRIPTION

Figure 1:
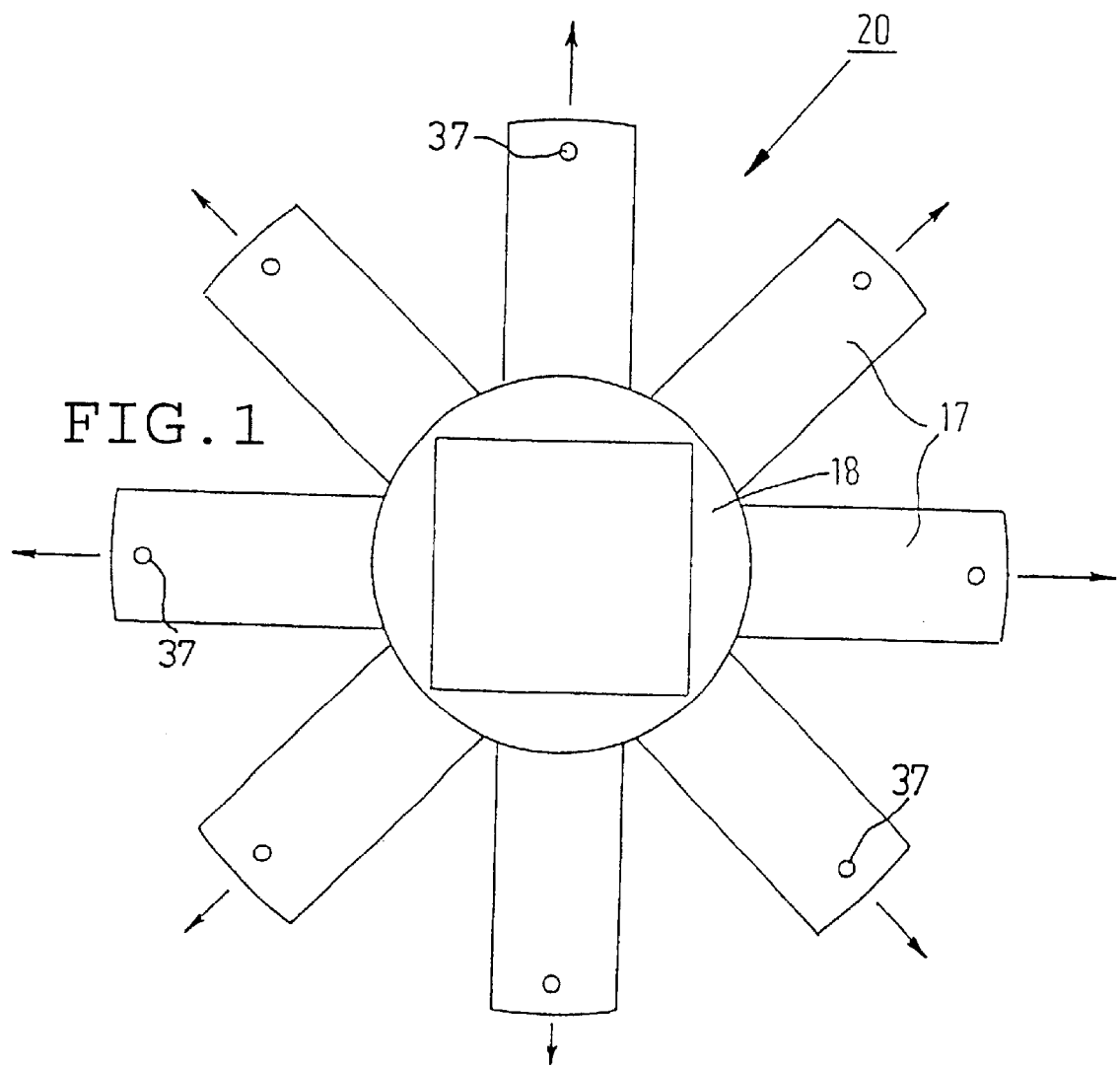
FIG. 1 shows the membrane connected to the arms according to the present invention, which can be used for increasing the distance between the skin grafts.
Figure 2:
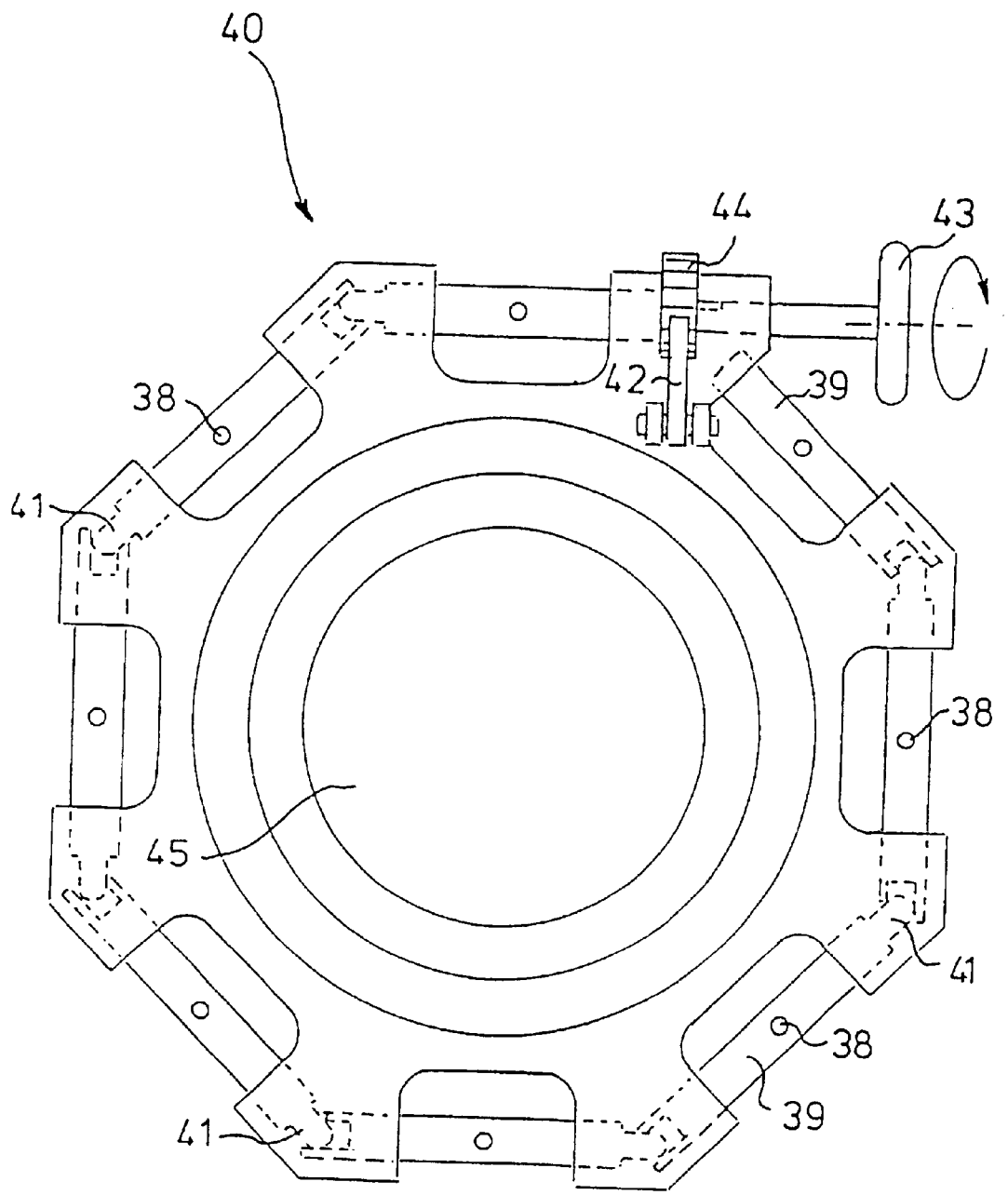
FIG. 2 shows the base member of the spreading means according to the present invention.

FIG. 1 shows the elastic membrane 18 to be used in spreading skin grafts in accordance with the method of the present invention. Assembly 20 comprises an elastic membrane 18, which is connected to eight arms 17 capable of movement in opposite directions in the same plane. The skin cut into skin grafts is transferred to elastic membrane 18. Once the skin grafts are present on elastic membrane 18 of assembly 20, the distance between the skin grafts is increased by moving arms 17 in opposite directions in the same plane, which is done by connecting arms 17 to cam 38 present on wind-up rod 39 of base member 40 shown in FIG. 2, using hole or aperture 37. The term spreading means is understood to mean the whole of assembly 20 and base member 40.

Base member 40 can be connected to assembly 20, which comprises arms 17 and membrane 18, whereby arm 17 is provided with hole 37, by placing hole 37 over a wind-up rod 39 provided with a cam 38. Base member 40 comprises a number of wind-up rods 39, which wind-up rods 39 are interconnected via connecting point 41. Rotating means 43, for example a ratchet wrench, can be rotated in the direction of the arrow shown in FIG. 2, causing the gear wheel 44 connected to rotating means 43 to drive wind-up rods 39. Locking member 42, which is connected to gear wheel 44, ensures that wind-up rods 39 remain in the desired position. The assembly 20 shown in FIG. 1 is placed on base 45 of base member 40, whereby holes 37 of arms 17 are connected to cam 38 of each wind-up rod 39. Rotation of rotating means 43 will result in arms 17, which are connected to wind-up rod 39 by means of hole 37 and cam 38, being wound on wind-up rod 39, as a result of which a force will be exerted on the assembly 20 of membrane 18 and arms 17. The exertion of this force on assembly 20 leads to the more elastic membrane 18 being stretched, as a result of which the distance between the skin grafts present on membrane 18 is increased.

Figure 3A:
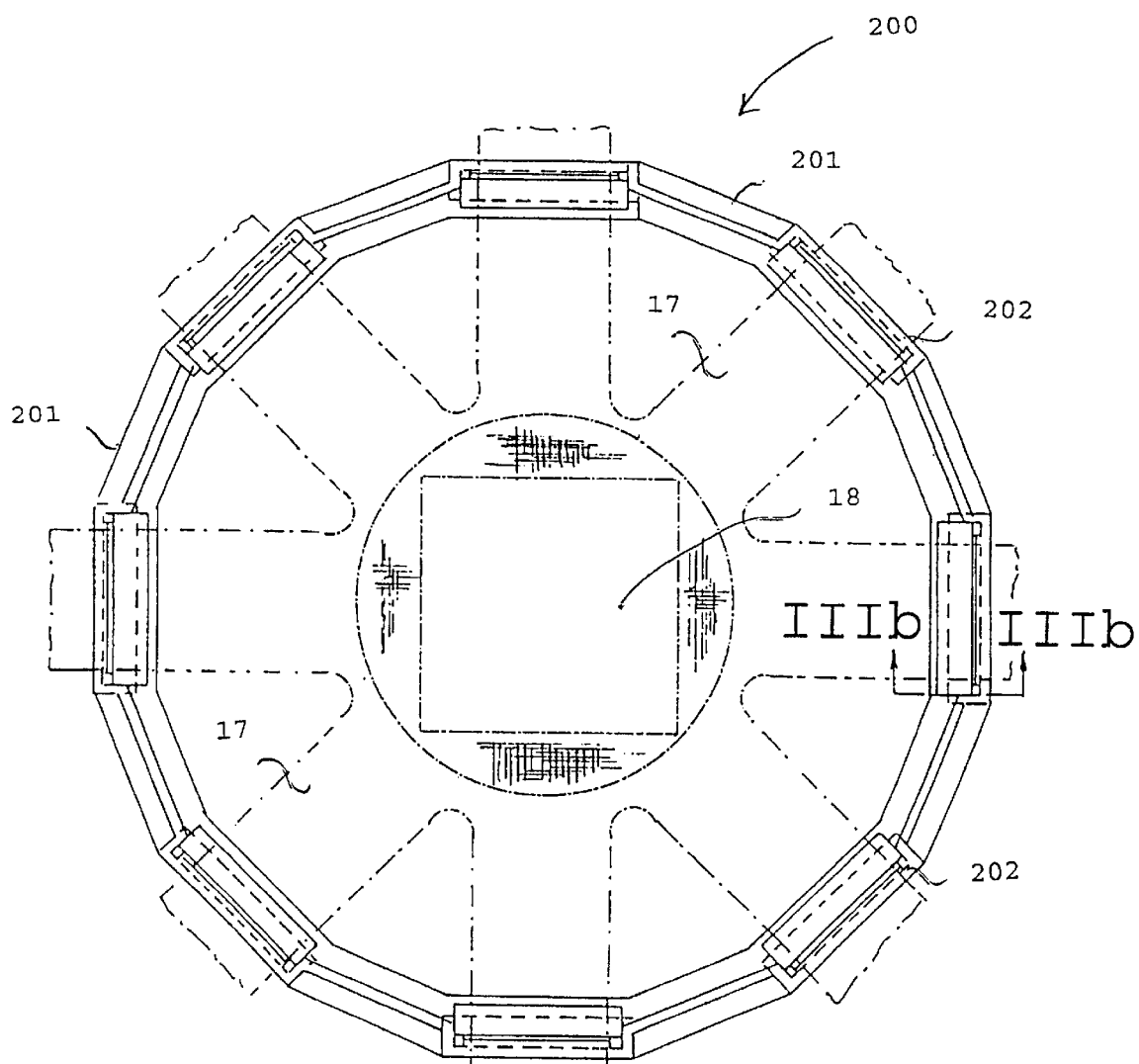
FIG. 3A shows the stretcher to be used in spreading skin grafts according to the present invention.
Figure 3B:
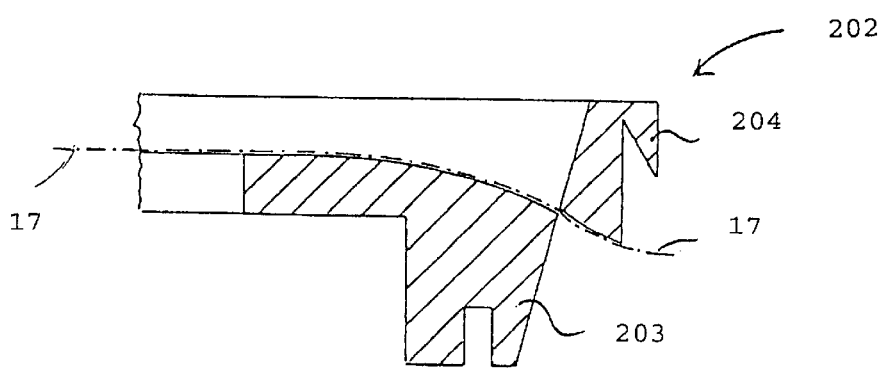
FIG. 3B shows the clamping means according to the stretcher as shown in FIG. 3A.

FIG. 3A shows the stretcher 200 to be used in spreading skin grafts. Stretcher 200 comprises a frame 201, in which clamping means 202 are arranged in regularly spaced-apart relationship. According to such an embodiment membrane 18, which is connected to arms 17, can be stretched in stretcher 200 by passing arms 17 through the clamping means 202 shown in FIG. 3B. Clamping means 202 comprises a base part 203 and a top part 204. When arm 17 is passed between base part 203 and top part 204 of clamping means 202, a particular clamping action is obtained as a result of the friction between the two parts, and the stretched condition of the assembly of membrane 18 and arms 17 will be retained. Stretcher 200 is placed on base member 40, arms 17 are passed between base part 203 and top part 204, hole 37 is connected to cam 38 of each wind-up rod 39, and then a spreading action as already described before is carried out. After achieving a sufficient spreading effect stretcher 200 is removed from base member 40 and clamping means 202 ensure that the stretched condition in stretcher 200 is retained. Then another stretcher 200 is placed on base member 40 and a number of skin grafts are spread in accordance with the above-described operation.

Once a desired distance between the skin grafts on elastic membrane 18 has been achieved, the skin grafts are transported, using a transport means operating at a sub-atmospheric pressure, for example. Said transport means is held with the side of apertured plate above the spread skin grafts present on the spreading means, after which a sub-atmospheric pressure is applied to the holding means by suitably adjusting the position of a changeover cock, which causes the skin grafts to adhere to the apertured plate. Then the skin grafts are then transported, for example to a burn, by the transport means. In a special embodiment a gauze of plastic material, more preferably donor skin, is provided over the spread skin grafts, which have been applied to a burn. In a special embodiment an adhesive is used in order to improve the adherence between the spread skin grafts and the material to be adhered. It is also possible, however, to transport spread skin grafts by means of tweezers, but it should be apparent that transporting each skin graft separately by means of tweezers is a very time-consuming activity. The number of skin grafts to be used with a burn generally amounts to a few dozen, so that it is preferred to transport the skin grafts by the above-described transport means.

Based on their experience and insight those skilled in this field are convinced that the healing process of a burn to which the skin grafts spread in accordance with the present invention have been applied, covered by donor skin, can be reduced by one week in comparison with the healing period obtained with the prior art methods.

What is claimed is:

1. A method for spreading skin grafts for application to a burn, characterized in that the skin grafts are placed on an elastic membrane (18), after which the membrane (18) is stretched in at least two directions in the same plane but substantially perpendicular to each other and the skin grafts present on the membrane (18) are spread.

2. A method according to claim 1, characterized in that a carrier used for forming skin grafts is used as the membrane (18).

3. A method for applying skin grafts to a burn, characterized in that a an adhering layer is placed on the spread skin grafts obtained in accordance with the method according to claim 1, after which the skin grafts adhering to said adhering layer are applied to the burn.

4. A method for applying skin grafts to a burn, characterized in that a gauze of plastic material is placed on the spread skin grafts obtained in accordance with the method according to claim 1, after which the skin grafts adhering to said plastic material are applied to the burn.

5. A method for applying skin grafts to a burn, characterized in that donor skin is placed on the spread skin grafts obtained in accordance with the method according to claim 1, after which the skin grafts adhering to said donor skin are applied to the burn.

6. A method for applying skin grafts to a burn, characterized in that the spread skin grafts according to claim 1 further includes the step of directly applying to the burn.

7. A spreading means to be used for increasing the distance between skin grafts, characterized in that said spreading means (20, 40) comprises an elastic membrane (18) which is connected to arms (17) which are capable of movement in at least two directions in the same plane, which arms (17) are made of a material which is less elastic than another material of which the membrane (18) is made, as well as a base member (40) which can be connected to said arms (17); and wherein movement of said arms in said at least two directions in the same plane increases the distance between skin grafts.

8. A spreading means according to claim 7, characterized in that said spreading means (20, 40) comprises four to eight arms (17) which are capable of movement in opposite directions in the same plane.

9. A membrane for spreading skin grafts by using a spreading means (20, 40) as disclosed in claim 17, characterized in that said membrane (18) consists of an elastic material having a rough surface.

10. A membrane according to claim 9, characterized in the said membrane (18) is made of a woven or knit material.

11. A spreading means to be used for increasing the distance between skin grafts, characterized in that said spreading means (20, 40) comprises an elastic membrane (18) which is connected to arms (17) which are capable of movement in at least two directions in the same plane, which arms (17) are made of a material which is less elastic than another material of which the membrane (18) is made, as well as a base member (40) which can be connected to said arms (17); and said base member (40) comprises wind-up means (39), which can be connected to the arms (17), which wind-up means (39) are capable of rotation, as a result of which the membrane (18) connected to the arms (17) can be stretched.

12. A spreading means to be used for increasing the distance between skin grafts, characterized in that said spreading means (20, 40) comprises an elastic membrane (18) which is connected to arms (17) which are capable of movement in at least two directions in the same plane, which arms (17) are made of a material which is less elastic than another material of which the membrane (18) is made, as well as a base member (40) which can be connected to said arms (17); and said arms (17) are connected to the base member (40) via a stretcher (200), in which said arms (17) can be clamped down.

13. A stretcher for spreading skin grafts by using a spreading means (20, 40) as disclosed in claim 21, characterized in that said stretcher(200) comprises a frame (201), in which at least two clamping means (202) are arranged in a regularly spaced-apart relationship, in which said membrane (18) and/or the arms (17) connected to said membrane (18) can be clamped down.

14. A stretcher according to claim 13, characterized in that said stretcher (200) comprises four to eight clamping means (202).

15. A stretcher according to claim 13, characterized in that said clamping means (202) comprises a base part (203) and a top part (204), whereby said base part (203) and said top part (204) exhibit a clamping action.

16. A method for spreading skin grafts, comprising:

connecting an elastic membrane (18) coupled to a plurality of arms (17) to a base member (40) further comprising a plurality of wind-up rods (39) wherein each arm (17) of said plurality of arms (17) is connected to a particular one of said plurality of wind-up rods (39);

placing a plurality of skin grafts on said membrane (18); and applying a force on said arms (17) by moving said arms (17) in an opposite direction in the same plane of said membrane (18) by winding each arm (17) on the particular wind-up rod (39) the arm (17) is connected to, thereby increasing the distance between the skin grafts present on said membrane (18).

* * * * *